United States Patent [19]
Rossman et al.

[11] Patent Number: 5,952,828
[45] Date of Patent: Sep. 14, 1999

[54] DRIVER DEVICE FOR MR ELASTOGRAPHY

[75] Inventors: Philip J. Rossman; Raja Muthupillai; Richard L. Ehman, all of Rochester, Minn.

[73] Assignee: Mayo Foundation for Medical Education and Research, Rochester, N.Y.

[21] Appl. No.: 08/915,828

[22] Filed: Aug. 21, 1997

Related U.S. Application Data

[60] Continuation-in-part of application No. 08/719,605, Sep. 25, 1996, which is a division of application No. 08/325,834, Oct. 19, 1994, Pat. No. 5,592,085.

[51] Int. Cl.⁶ .................................................. G01V 3/00
[52] U.S. Cl. .................................................. 324/318
[58] Field of Search .................................. 324/318, 322, 324/315, 307, 309

[56] References Cited

U.S. PATENT DOCUMENTS

| | | | |
|---|---|---|---|
| Re. 32,701 | 6/1988 | Moran | 324/309 |
| 4,543,959 | 10/1985 | Sepponen | 324/309 |
| 5,131,392 | 7/1992 | Jolesz et al. | 324/309 |
| 5,284,144 | 2/1994 | Delannoy et al. | 324/315 |

*Primary Examiner*—Louis Arana
*Attorney, Agent, or Firm*—Quarles & Brady LLP

[57] ABSTRACT

Devices for applying an oscillatory stress to an object positioned in a polarizing magnetic field of an NMR imaging system are used to perform MR elastography. The devices employ electrically energized coils which are connected to drive members and drive plates in a manner to provide various oscillatory forces to an object being imaged. The different oscillatory forces enable different body organs to be imaged using MR elastography methods.

19 Claims, 6 Drawing Sheets

DRIVER DEVICE FOR MR ELASTOGRAPHY

CROSS REFERENCE TO RELATED APPLICATIONS

This application is a continuation-in-part of application Ser. No. 08/719,605 filed Sep. 25, 1996 which is a division of application Ser. No. 08/325,834 filed Oct. 19, 1994, now U.S. Pat. No. 5,592,085.

BACKGROUND OF THE INVENTION

The field of the invention is nuclear magnetic resonance imaging methods and systems. More particularly, the invention relates to devices for implementing MR elastography.

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging ("MRI") systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (e.g. of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant γ of the nucleus). Nuclei which exhibit this phenomena are referred to herein as "spins", and materials which contain such nuclei are referred to herein as "gyromagnetic".

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment $M_t$, which is rotating, or spinning, in the xy plane at the Larmor frequency. The practical value of this phenomenon resides in the signal which is emitted by the excited spins after the excitation signal $B_1$ is terminated. There are a wide variety of measurement sequences in which this nuclear magnetic resonance ("NMR") phenomena is exploited.

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well known reconstruction techniques. To perform such a scan, it is, of course, necessary to elicit NMR signals from specific locations in the subject. This is accomplished by employing magnetic fields ($G_x$, $G_y$, and $G_z$) which are superimposed on the polarizing field $B_0$, but which have a gradient along the respective x, y and z axes. By controlling the strength of these gradients during each NMR cycle, the spatial distribution of spin excitation can be controlled and the location of the resulting NMR signals can be identified.

It is well known that NMR can be used to detect and image the movement of spins. As disclosed in U.S. Pat. No. Re. 32,701 entitled "NM Scanner With Motion Zeugmatography", acquired NMR signals can be sensitized to detect moving spins by applying a bipolar magnetic field gradient at the proper moment in each NMR measurement sequence. The phase of the resulting NMR signal measures the velocity of spins along the direction of the motion sensitizing magnetic field gradient. With more complex motion sensitizing magnetic field gradients, higher orders of motion, such as acceleration and jerk can also be measured with this method.

It has been found that MRI imaging can be enhanced when vibrational energy is applied to the object being imaged in a method called MR elastography.

SUMMARY OF THE INVENTION

The present invention relates to the imaging of mechanical characteristics of an object, and more particularly, to vibration devices for applying an oscillatory stress to an object positioned in the polarizing magnetic field of an NMR imaging system in order to practice MR elastography.

The vibration device includes a supporting member positioned adjacent the object and in the polarizing magnetic field. An arm is fastened to the supporting member and extends outward therefrom. At least one coil of conductive wire is mounted to the arm and has a pair of terminals for electrical connection to a current source. An applicator is connected to the arm and shaped to mechanically couple motion of the arm to the object. The arm is set in oscillatory motion by the application of an oscillating current to the coil terminals which interacts with the magnetic field of the NMR system.

In one embodiment, the arm is flexible. In another embodiment, the arm is a drive shaft and is pivotally connected to the support member. In one embodiment, a single drive coil effects a linear or lateral motion to a drive shaft and an object contacting member, and in yet another embodiment, two drive coils effect a reciprocating motion to a drive shaft and an object contacting member. In still another embodiment, the two drive coils effect a reciprocating motion to two drive shafts to cause a reciprocating motion to a pair of human breasts.

A general object of the invention is to provide devices for applying an oscillatory stress directly to an object positioned in the polarizing magnetic field of an NMR imaging system in synchronism with an applied alternating gradient field.

Still another object of the invention is to provide devices of the foregoing kind wherein the oscillatory stress is applied to the object to be imaged as a compressive force, shear force or reciprocating force.

The foregoing and other objects and advantages of the invention will appear from the following description. In the description, reference is made to the accompanying drawings which form a part hereof, and in which there is shown by way of illustration, preferred embodiments of the invention. Such embodiments do not necessarily represent the full scope of the invention, however, and reference is made therefore to the claims herein for interpreting the scope of the invention.

GENERAL DESCRIPTION OF THE INVENTION

The physical properties of tissue are measured by applying a stress (e.g. tension, pressure, or shear) and observing the resulting strain (e.g. elongation, compression, rotation). By measuring the resulting strain, elastic properties of the tissue such as Young's modulus, Poisson's ratio, the shear modulus, and the bulk modulus, can be calculated. By applying the stress in all three dimensions and measuring the resulting strain, the elastic properties of the tissue can be completely defined.

By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

The present invention is employed in a system such as that described in the above-cited U.S. Pat. No. 5,592,085 which provides a means for measuring the strain in gyromagnetic materials such as tissues using NMR methods and apparatus. The Larmor equation is given by $$\omega = \gamma \overline{B}$$

where $\omega$ is the angular resonant frequency of the NMR signal produced by spins having a characteristic gyromagnetic ratio of $\gamma$ when placed in a magnetic field having a density and direction $\overline{B}$. The magnetic field vector $\overline{B}$ can be broken down into two components $$\overline{B} = \overline{B}_0 + r\overline{G}_r$$

where $B_0$ is the polarizing magnetic field, r is the location of the spins, and $G_r$ is the magnetic field gradient.

Since the angular frequency of the NMR signals produced by the spins is the rate of change of their phase, the phase of the spin signals as a function of time is as follows:

$$\phi(t) = \int \omega(t) dt.$$

Substituting equation (1), the relationship between NMR signal phase and the applied gradient field is obtained $$\phi(t) = \gamma \int G(t') r(t') dt',$$

where G and r are expressed as functions of time (t') for obtaining a general expression of the Larmor equation. This equation indicates that the NMR signal produced by moving spins will accrue a phase shift relative to that accrued by static spins when in the presence of a magnetic field gradient.

If an oscillating stress is applied to tissue along the direction r at an angular frequency $\omega_p$, a wave is launched and spins are displaced by amounts determined by the elastic properties of the tissue. If it is assumed that this propagation occurs without loss, the displacement ($\Delta$) of spins at location (r) may be expressed as follows:

$$\Delta = \Delta_0 \cos(\omega_p t + kr + \theta),$$

where $\Delta_0$ is the maximum displacement produced by the applied stress, k is the wave number, and $\theta$ is the phase offset of the spin displacement relative to the applied oscillating stress. The wave number k is equal to $2\pi$ radians divided by the wavelength ($\lambda$) of the propagated wave, and if it is assumed that the spin displacement occurs for just one cycle (t=0 to T) of the applied oscillating stress, then the NMR signal produced by the spin will accumulate a phase indicated by the following expression:

$$\phi(t) = \gamma \int_{t=0}^{t=T} G(t') \Delta_0 \cos(\omega_p t + kr + \theta) dt'$$

If the magnetic field gradient G(t') is constant during this time period; no phase signal will be accumulated. However, if the magnetic field gradient G(t') is synchronized with the applied stress and is switched in polarity half way through the time period (T), the phase of the NMR signal ($\phi$) at the completion of the time period will be proportional to the displacement of the spins. This displacement along the r direction is the strain which results from the applied stress along the same direction r.

NMR measurements can be made with imaging gradients applied, and a strain image indicative of the longitudinal strain at each pixel may be reconstructed. This strain image has pixel values as follows:

$$S_L(t,r) = \Delta_0 \cos(\omega_p t + kr).$$

If the measurement is repeated with the oscillating stress in the same direction, but with the alternating gradient G(t') oriented along each of the orthogonal axes, the displacements, along these axes can be determined and the orthogonal strain ($S_T$) calculated. From this information Poisson's ratio ($\sigma$) can be calculated as follows:

$$\sigma = S_T/S_L$$

Further information can be learned about the elastic properties of tissues by changing the phase relationship of the applied oscillatory stress and the synchronized alternating motion gradient. For example, if the phases are offset $\pi/2$ radians, a second strain image $S_0$ is produced having the following pixel values:

$$S_0(t, r) = \Delta_0 \cos(\omega_p t + kr + \pi/2)$$
$$= \Delta_0 \sin(\omega_p t + kr)$$

The gradient in each of the strain images $S_L$ and $S_0$ may be defined as follows:

$$\nabla S_L = \frac{\partial S_L}{\partial_x}\vec{i} + \frac{\partial S_L}{\partial_y}\vec{j}$$

$$\nabla S_0 = \frac{\partial S_o}{\partial_x}\vec{i} + \frac{\partial S_o}{\partial_y}\vec{j}$$

Using these gradients, the wave number (k) of the propagated wave at each image pixel can be calculated as follows:

$$k = \sqrt{|\nabla S_L| \cdot |\nabla S_L| + |\nabla S_0| \cdot |\nabla S_0|} \bigg/ \sqrt{S_0^2 + S_L^2}$$

Knowing the frequency (f) of the applied oscillatory stress, the propagation velocity (c) can then be calculated at each image pixel as long as the viscosity effects are not significant.

$$\lambda = 2\pi/k$$
$$c = f\lambda$$

If the density ($\rho$) of the gyromagnetic medium is known, the propagation velocity (c) can be used to calculate Young's modulus (Y):

$$Y = c^2\rho.$$

Since compliance is the inverse of Young's modulus (i.e.1/Y), the compliance of the gyromagnetic medium may also be calculated. An image in which pixel intensity is determined by the calculated compliance has diagnostic value in medicine because such an image displays what a physician feels when manually palpating tissue. With the knowledge of Poisson's ratio ($\sigma$) and the Young's modulus (Y) all other values of moduli, namely the shear modulus ($\mu$) and the bulk-modulus ($\beta$) may be calculated, since only two of these four elastic properties are actually independent. Bulk modulus ($\beta$) can be expressed from Young's modulus and Poissons ratio, in the following way:

$$Y = 3\beta(1 - 2\sigma).$$

Shear Modulus ($\mu$) can be expressed as follows:

$$Y = 2\mu(1 + \sigma).$$

It should be apparent that the oscillatory stress may be applied in three orthogonal directions and the synchronized gradient field may also be applied in three separate orthogonal directions for each applied stress direction. Spin displacements ($\Delta, \eta, \Sigma$) in all three directions may be measured, and all the components of the strain dyadic (second-rank tensor field), given in the following matrix may be measured:

$$\begin{pmatrix} \frac{\partial \nabla}{\partial x} & \frac{\partial \eta}{\partial x} & \frac{\partial \Sigma}{\partial x} \\ \frac{\partial \Delta}{\partial y} & \frac{\partial \eta}{\partial y} & \frac{\partial \Sigma}{\partial y} \\ \frac{\partial \nabla}{\partial z} & \frac{\partial \eta}{\partial z} & \frac{\partial \Sigma}{\partial z} \end{pmatrix}$$

With these measurements it is possible to characterize all the elastic properties of the gyromagnetic medium under investigation using the above-described calculations.

DESCRIPTION OF THE PREFERRED EMBODIMENTS

Figure 1A:
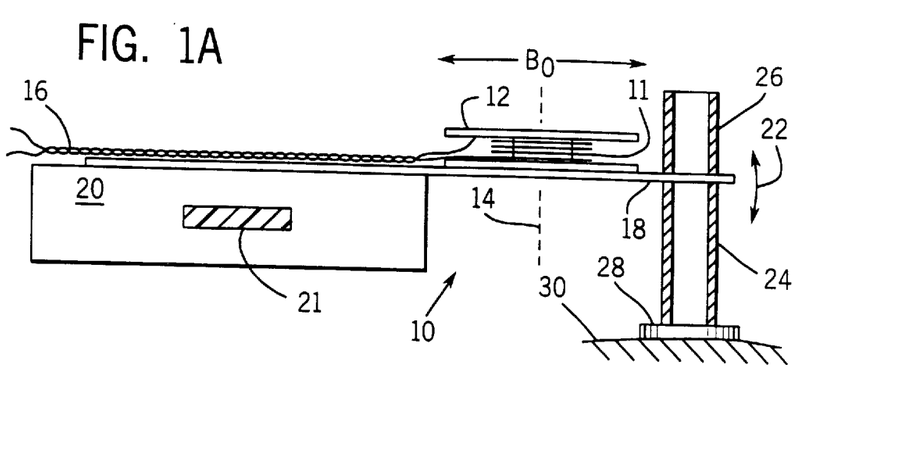
FIGS. 1A and 1B are elevation and top views respectively of a first embodiment of the transducer that is used to practice the present invention.
Figure 1B:
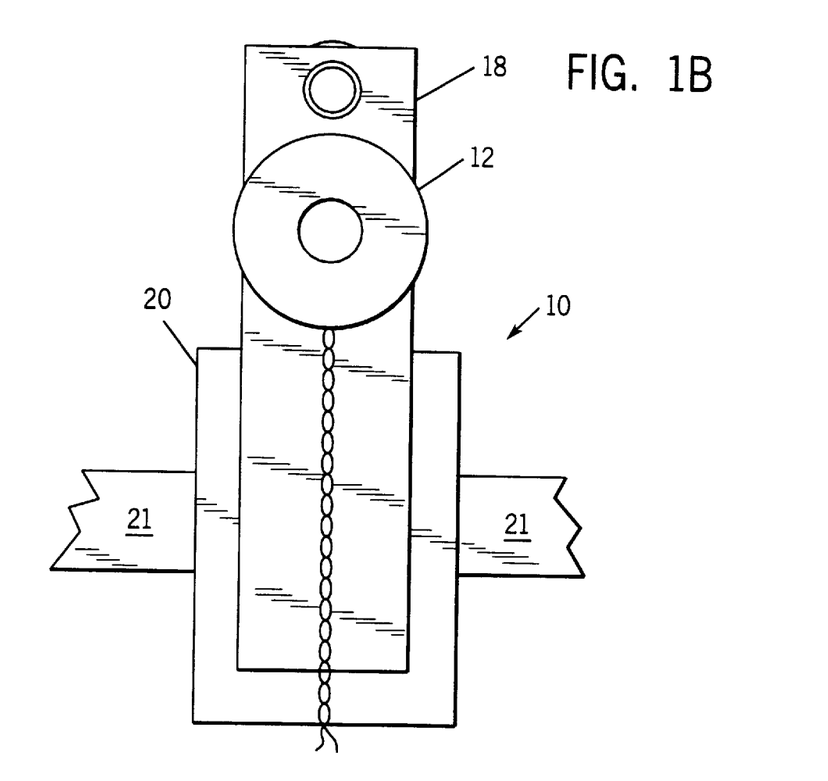

Referring particularly to FIGS. 1A and 1B, one embodiment of the invention employs a transducer 10 suitable for applying an oscillatory stress externally to a patient. This transducer is utilized in conjunction with the NMR system described in the above referred to U.S. Pat. No. 5,592,085 which is hereby incorporated by reference. The transducer 10 includes a coil of wire 11 wound on a bobbin 12, with the coil axis 14 directed perpendicular to the polarizing magnetic Field $B_0$. The coil 11 is preferably 400 turns of 30 AWG. copper wire, and its leads 16 are connected directly to an amplifier as described in the above patent. Any coil which is wound until the impedance is 8 $\Omega$ could be employed. The bobbin 12 is mounted to a flexible arm 18 that is attached to, and cantilevered from a supporting block 20. When a current passes through the coil 11, the magnetic field which it produces interacts with the polarizing field $B_0$ of the MRI system. The bobbin 12 is thus twisted to bend the flexible arm 18 either upward or downward depending on the direction of current flow. By alternating the direction of current flow, the coil 11 twists back and forth to produce a corresponding alternating force which causes the flexible arm 18 to oscillate as indicated by the arrow 22. A strap 21 extends through an opening in the supporting block 20 and securely fastens it to the patient.

The oscillatory motion of the arm 18 is coupled to the subject 30 by an applicator 24. In its simplest form the applicator 24 is comprised of a tube 26 of the desired length which is secured at one of its ends to the arm 18. A pressure plate 28 is secured to the other end of the tube 26. The pressure plate 28 rests on the subject 30 to be imaged and its oscillatory movement produces a corresponding oscillatory compressive force that generates the desired synchronous motion.

Other transducers 110, 210, 310, 410 and 510 are depicted in FIGS. 2, 3, 4A, 4B, 5A, 5B, 6A and 6B. Similar numbers are employed to designate similar components except they are numbered in the "100," "200," "300," "400" and "500" series respectively. All of the transducers 110, 210, 310, 410 and 510 work on the principle that a loop of wire with a given area and disposed in a constant magnetic field ($B_0$) will experience a net torque when it conducts a current, and this torque can be controlled to produce the desired oscillatory stress.

Figure 2:
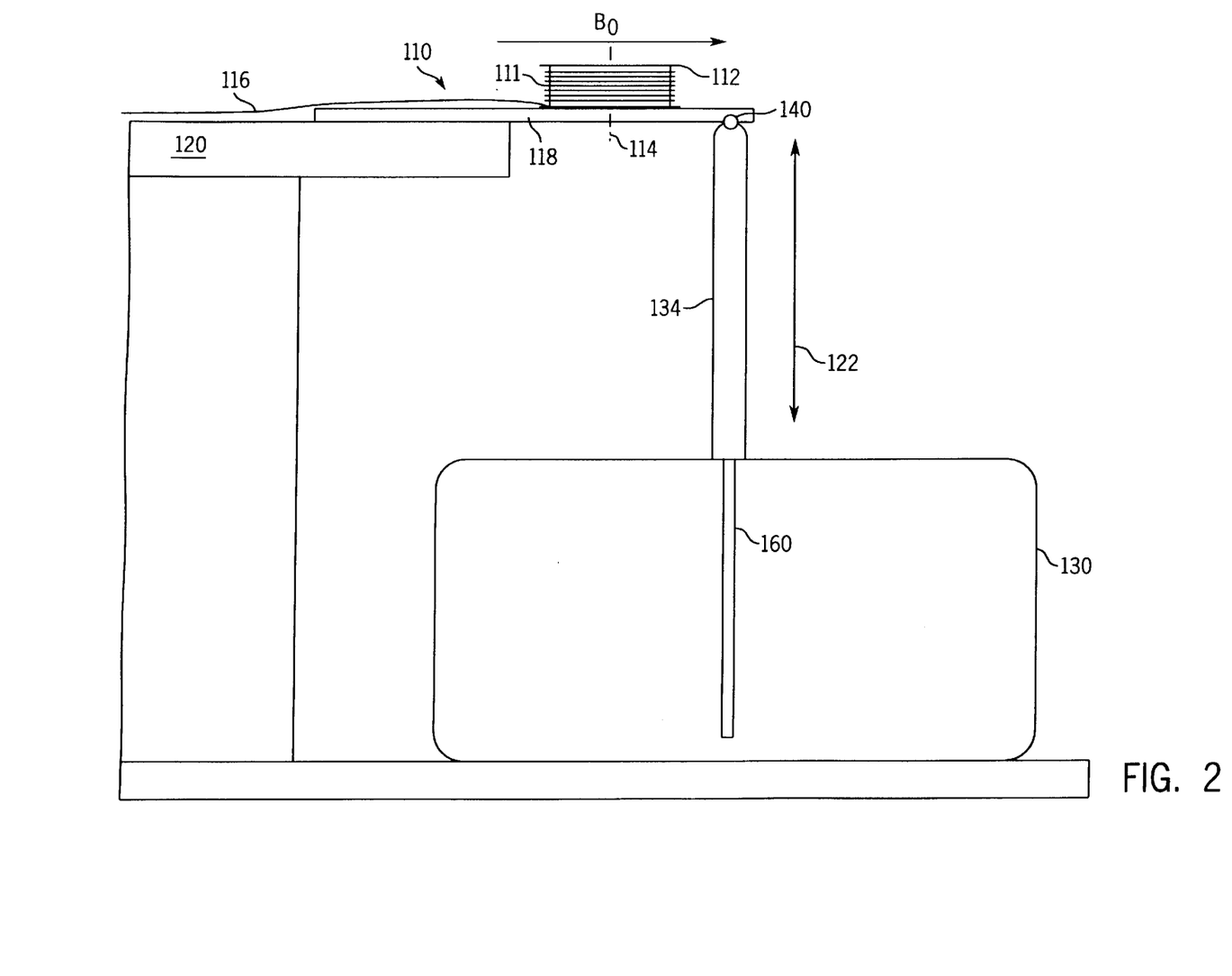
FIGS. 2, 3, 4A, and 5A are elevation views of additional embodiments of the transducer, with FIGS. 4B and 5B representing top views of FIGS. 4A and 5A, respectively.

As seen in FIG. 2 the transducer 110, is similar to the transducer 10 described above, but it couples to the object 130 in a different manner. It includes a rod or needle 160 that extends from a driving shaft 134 which is pivotally attached to arm 118 by pin 140 and moves as indicated by directional arrow 122. The applicator rod or needle 160 can be inserted into an opening in the subject 130 to rest against a particular structure (such as the prostate gland), or it may be inserted through tissue and its end anchored to an internal structure (such as the liver). Many shapes and sizes are possible.

Figure 3:
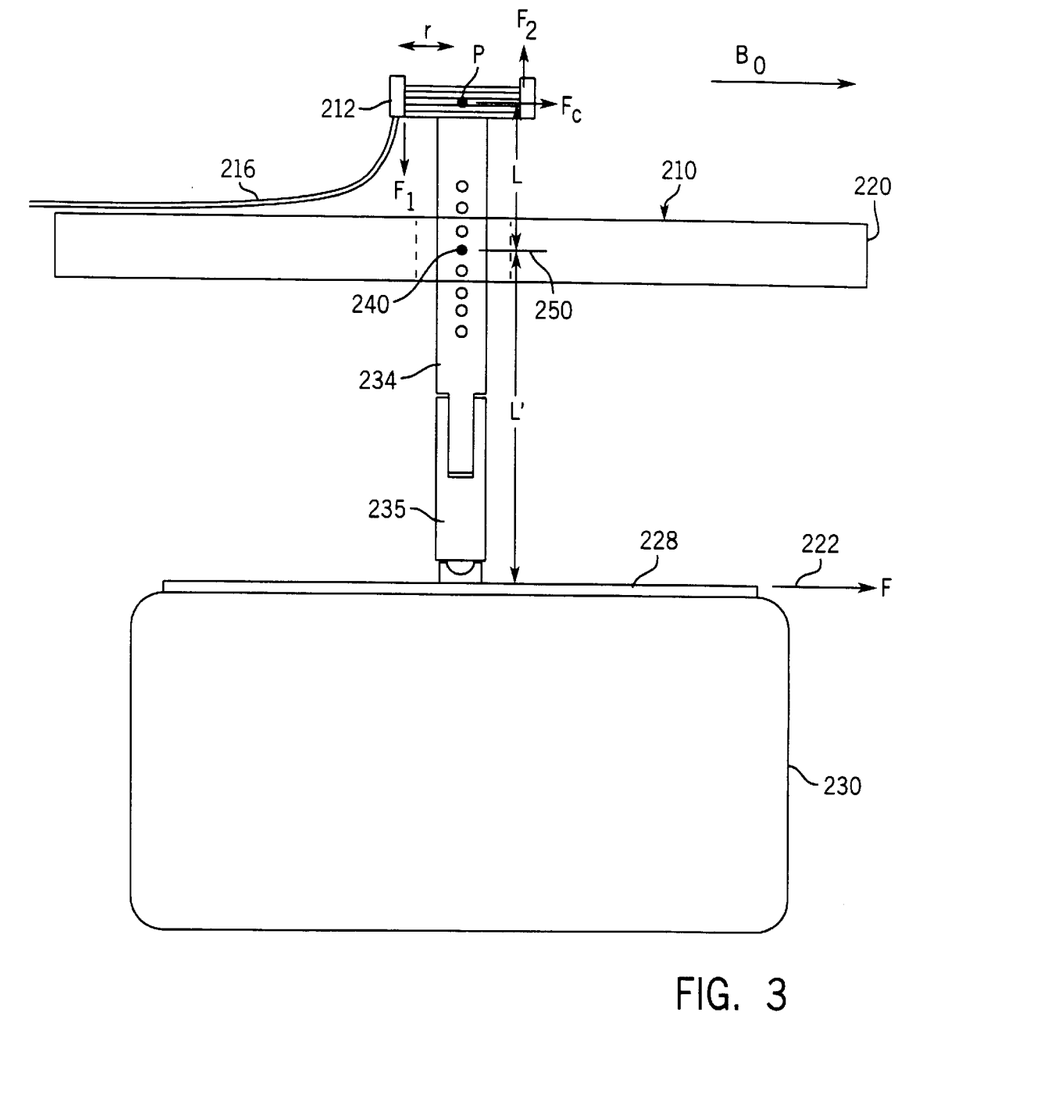

Referring to FIG. 3, transducer 210 effects a lateral motion on contact plate 228 as indicated by directional arrow 222. This force emanates from a coil 212 which receives a driving current through wires 216. This coil 212 interacts with the polarizing field $B_0$ to produce a torque. The direction of the induced torque vector is normal to both $B_0$ and the axis of rotation P of the coil 212. The coil has a radius r and a net torque is produced by the vertical forces $F_1$ and $F_2$ acting on the coil 212 about its axis of rotation P. Because the coil 212 is rigidly attached to a shaft 234, this torque is converted to a plate force $F_c$ as this shaft 234 pivots about the axis 240. Drive shaft 234 is connected to linkage rod 235 which drives contact plate 228 in the direction of arrow 222. When an alternating current is applied to the coil 212, the plate 228 moves back and forth to apply an oscillating shear stress to the object 230. The extent of this movement can be adjusted by changing the pivot axis 240 to alter the lengths L and L' or by changing the maximum amplitude of the alternating current passing through the coil 212.

Figure 4A:
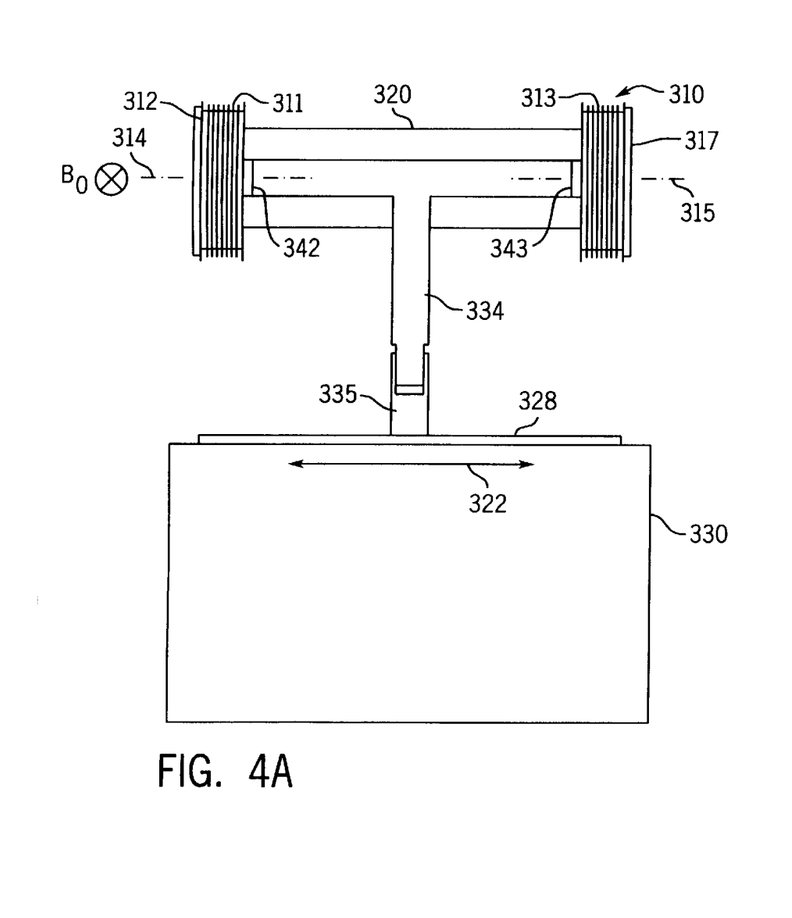
Figure 4B:
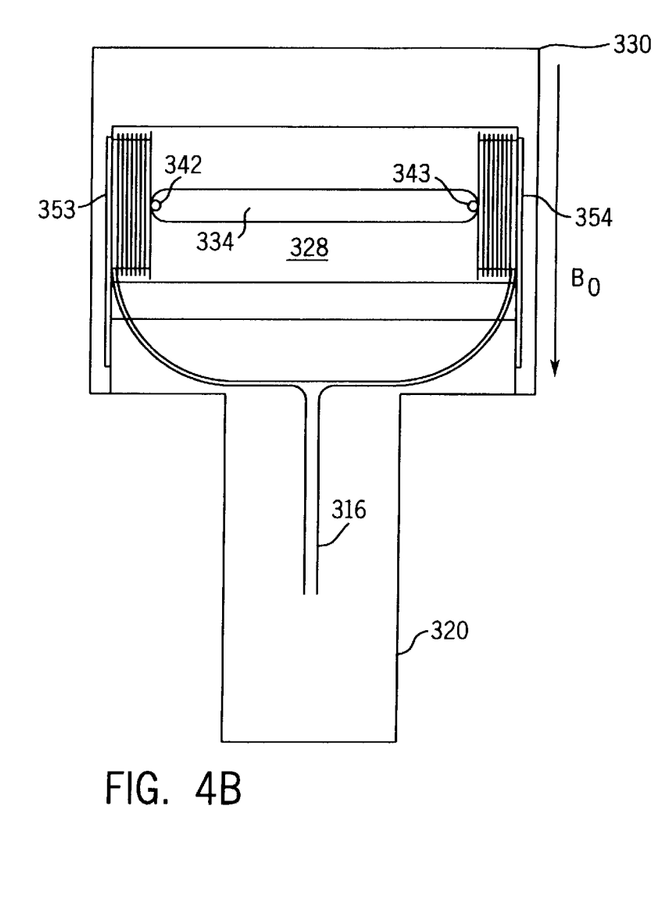

FIGS. 4A and 4B depict a transducer 310 which can effect a dual transverse motion on contact plate 328 to apply an oscillating shear stress to sample 330. Dual coils 311 and 313, and their respective bobbins 312 and 317, are connected to a T-shaped drive shaft 334 at pivot points 342 and 343. Flexible connectors 353 and 354 provide connection of the coils 311 and 313 to a support or mounting block 320. It provides structural support and an anchor point for the flexible connectors 353 and 354. Drive shaft 334 engages linkage rod 335 which moves the contact plate 328 and the sample or subject 330 in a direction indicated by arrow 322. When an alternating current is applied to coils 311 and 313, a transverse motion is effected that is orthogonal to the main magnetic field $B_0$. In this instance the motion is in the "X" direction or from left to right in the bore of the magnet. In order for any motion to occur the central axis of each drive coil 311 and 313 must be oriented at a right angle to $B_0$. Transducer 310 has two such coils 311 and 313. The design of the linkage between the two coils restricts the motion of the contact plate 328 to the direction indicated by arrow 322.

Figure 5A:
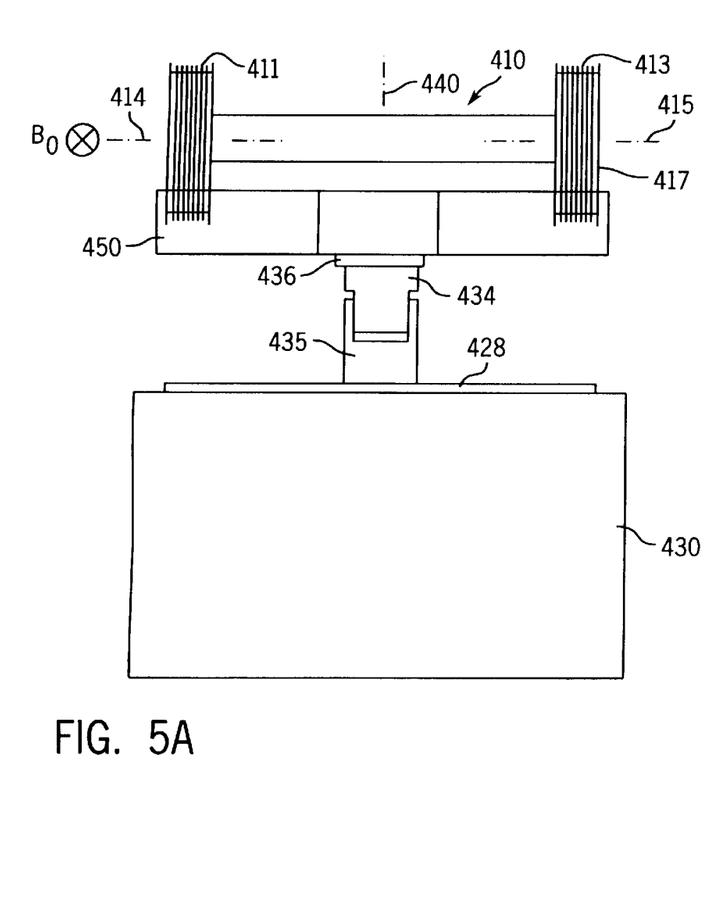
Figure 5B:
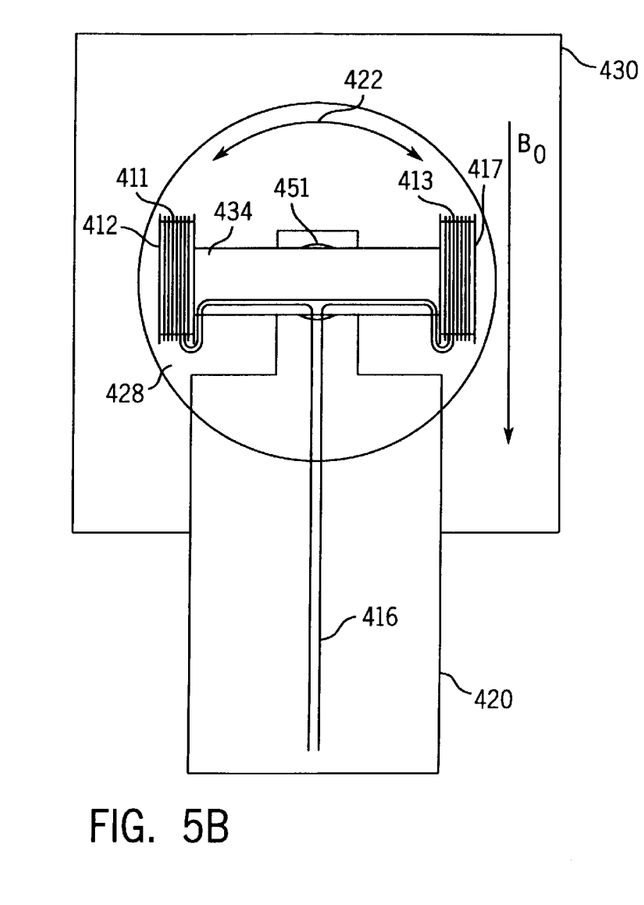

Transducer 410 shown in FIGS. 5A and 5B also employs two coils 411 and 413. However, they are mounted on a rotating drive shaft 434 which in turn is mounted on a bushing 436 in frame 420. Drive current is applied to coils 411 and 413 to produce a torque about the axis 440. This torque is coupled to a drive plate 428 through T-shaped drive shaft 434 connected to linkage rod 435. When an alternating current is applied to the coils 411 and 413, the drive plate 428 is rotated in a reciprocating motion as illustrated by directional arrow 422. A mounting block 420 having a cavity 451 accommodates drive shaft 434 with coils 411 and 413.

Figure 6A:
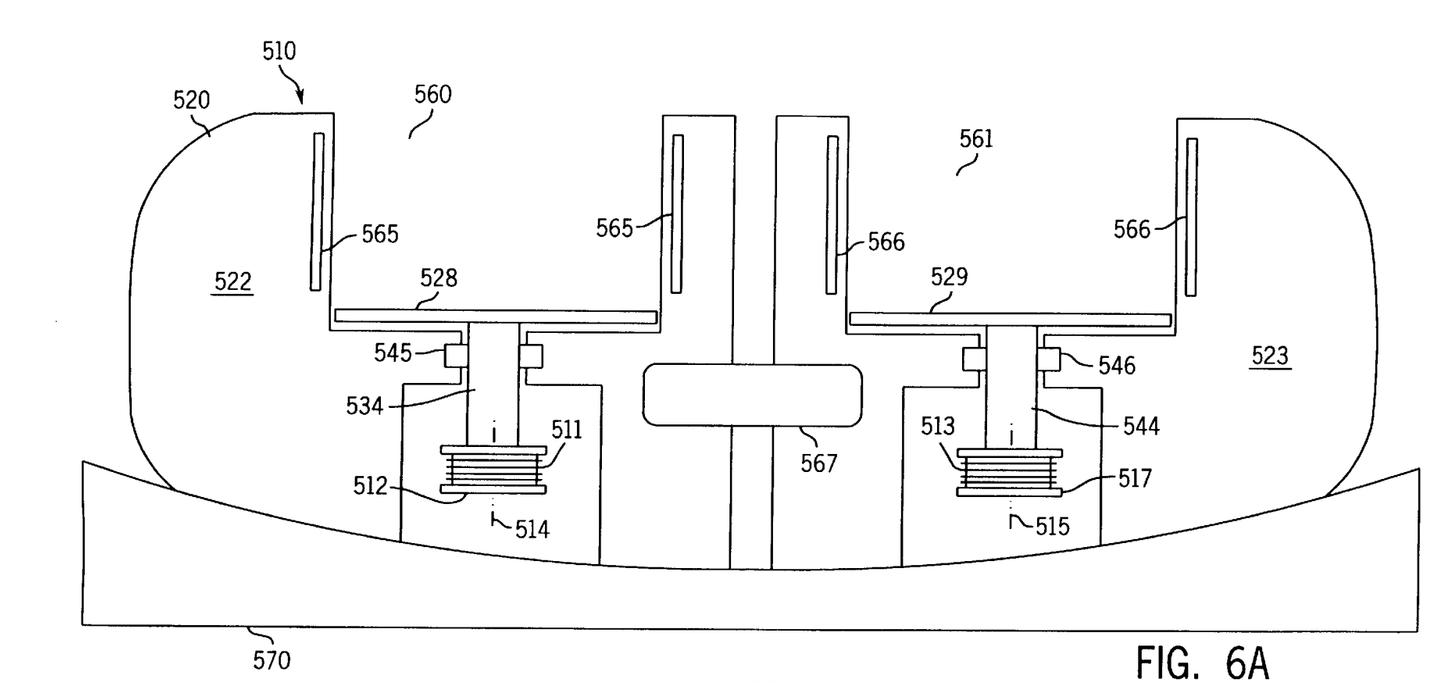
FIG. 6A is a top view of an additional embodiment with FIG. 6B illustrating the motion of the FIG. A embodiment.
Figure 6B:
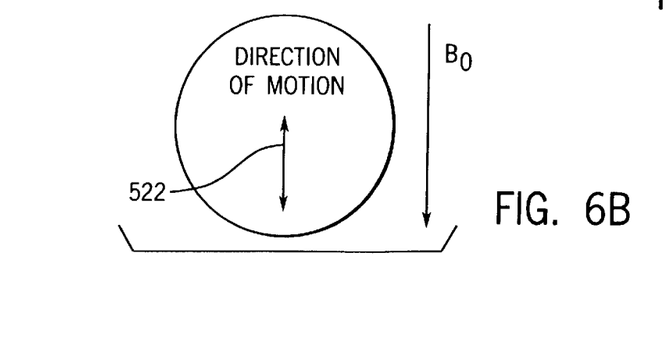

FIG. 6A illustrates a transducer 510 which is designed to accommodate a pair of human breasts. For this purpose, it has two breast receiving compartments 560 and 561 each including contact plates 528 and 529, respectively, for effecting an oscillating motion thereto as shown by direction arrow 522 in FIG. 6B. A pair of MRI coils 565 and 566 are oppositely disposed in the respective compartments 560 and 561. These coils can be of many types of MRI RF coils such as "receive-only" surface coils, "receive-only" phased array multicoils, "transmit-receive" quadrature coils, etc. This design does not restrict the use of any type of MRI imaging RF coil. Drive shafts 534 and 544 are pivotally connected to support frame sections 522 and 523, respectively, of support frame 520 by the pivot pins 545 and 546. The frame sections 522 and 523 are interconnected by the flexible coupling 567. A patient support table is shown at 570.

All elements of the transducers 10, 110, 210, 310, 410 and 510 are constructed using non-magnetic materials. Thermoplastics such as acrylic may be used, for example, because such materials can be molded or machined into many desired shapes, and they are relatively benign to the tissues which they contact. Magnetic materials could also possibly be employed.

For some applications it may be possible to produce the alternating gradient field pulses as described in U.S. Pat. No. 5,592,085 with the same transducers 10, 110, 210, 310 and 410 used to apply stress to the subject. In this case, the indicated transducers include a coil that acts as a local gradient coil for adjacent tissues. The same alternating current applied to this coil to produce the alternating magnetic field gradient pulses also causes the coil to move in an oscillatory manner at the same frequency and phase. Such coil might be used, for example, to detect tumors in the prostrate gland.

While in several of the embodiments there are single coils described for activating the arms and applicators, it is obvious that two or more coils could be employed in conjunction with two or more arms and applicators to effect different phase relationships, such as by the electrical or mechanical means, and the direction of the propagating or resulting wave.

We claim:

1. A device for applying an oscillatory stress to an object positioned in the polarizing magnetic field of an NMR imaging system, the combination comprising:

a supporting member positioned adjacent the object and in the polarizing magnetic field;

an arm fastened to the supporting member and extending outward therefrom;

a coil of conductive wire mounted to the arm and having a pair of terminals for electrical connection to a current source; and an applicator connected to the arm and shaped to mechanically couple motion of the arm to the object; and wherein the arm is set in oscillatory motion by the application of an oscillating current to the coil terminals.

2. The device as recited in claim 1, in which the arm is flexible.

3. The device as recited in claim 1, in which the arm is a drive shaft.

4. The device as recited in claim 3, in which the arm is pivotally connected to the support member.

5. The device as recited in claim 3, in which there are two coils connected to the drive shaft in an opposing manner constructed and arranged to effect a pivotal motion to the drive shaft and the applicator is a contact member connected to the drive shaft for contact with the object.

6. The device as recited in claim 3, in which there are two coils connected to the drive shaft in an opposing manner constructed and arranged to effect a reciprocating motion to the drive shaft and the applicator is a contact member connected to the drive shaft for contact with the object.

7. The device as recited in claim 6, in which the coils are also flexibly connected to a mounting member.

8. The device as recited in claim 1, in which the applicator includes a contact member and is shaped for insertion into the object.

9. A device for applying an oscillatory stress to an subject positioned in the polarizing magnetic field of an NMR imaging system, the combination comprising:

a supporting member positioned adjacent the subject and in the polarizing magnetic field;

a flexible arm-fastened to the supporting member and extending outward therefrom;

a coil of conductive wire mounted to the flexible arm and having a pair of terminals for electrical connection to a current source; and an applicator connected to the flexible arm and shaped to mechanically couple motion to the flexible arm to the subject; and wherein the arm is set in oscillatory motion by the application of an oscillating current to the coil terminals.

10. The device as recited in claim 9, in which the applicator is shaped to press against the surface of the subject.

11. The device as recited in claim 9, in which the applicator is shaped for insertion into an opening in the subject.

12. The device as recited in claim 9, in which the applicator is shaped for insertion into the subject.

13. A device for applying an oscillatory stress to the breasts of a subject positioned in the polarizing magnetic field of an NMR imaging system, the combination comprising:

a supporting member defining a compartment to receive a human breast;

an arm connected to the supporting member and having one end extending into the compartment;

a coil of conductive wire mounted to the arm;

an applicator disposed in the compartment and connected to said one end of the arm to mechanically couple motion of the arm to the breast; and wherein the arm is set in oscillatory motion by the application of an oscillating current to the coil terminals.

14. The device as recited in claim 13, in which the arm is pivotally connected to the support member.

15. The device as recited in claim 13, wherein an MRI coil is mounted to the support member and disposed adjacent the compartment.

16. The device as recited in claim 15, wherein the MRI coil encircles the compartment.

17. The device as recited in claim 13, in which the applicator is a plate member that extends substantially across the bottom of the compartment.

18. The device as recited in claim 13, further including a second compartment, a second arm connected to the supporting member having one end extending into the second compartment and a coil of conductive wire mounted to the arm, wherein the compartments receive two breasts.

19. The device as recited in claim 18, in which the support member is constructed in two sections and connected by a flexible coupling.

* * * * *